United States Patent
Roessl et al.

(10) Patent No.: US 10,420,521 B2
(45) Date of Patent: Sep. 24, 2019

(54) GRATING DEVICE FOR AN X-RAY IMAGING DEVICE

(71) Applicant: KONINKLIJKE PHILIPS N.V., Eindhoven (NL)

(72) Inventors: Ewald Roessl, Ellerau (DE); Thomas Koehler, Norderstedt (DE); Hans-Aloys Wischmann, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 142 days.

(21) Appl. No.: 15/328,086

(22) PCT Filed: Jul. 20, 2015

(86) PCT No.: PCT/EP2015/066554
§ 371 (c)(1),
(2) Date: Jan. 23, 2017

(87) PCT Pub. No.: WO2016/020178
PCT Pub. Date: Feb. 11, 2016

(65) Prior Publication Data
US 2017/0202528 A1    Jul. 20, 2017

(30) Foreign Application Priority Data
Aug. 5, 2014 (EP) .................................. 14179793

(51) Int. Cl.
A61B 6/00 (2006.01)
G21K 1/06 (2006.01)
(Continued)

(52) U.S. Cl.
CPC .............. *A61B 6/4291* (2013.01); *A61B 6/06* (2013.01); *A61B 6/484* (2013.01); *G21K 1/06* (2013.01);
(Continued)

(58) Field of Classification Search
CPC ........... A61B 6/00; A61B 6/06; A61B 6/4291; A61B 6/484; A61B 6/4417; A61B 6/44; G01N 23/20075
(Continued)

(56) References Cited

U.S. PATENT DOCUMENTS

| 4,663,774 A | 5/1987 | Saffer |
| 6,809,465 B2 | 10/2004 | Jin |

(Continued)

FOREIGN PATENT DOCUMENTS

| CN | 102096349 A | 6/2011 |
| WO | 2012/029005 | 3/2012 |

OTHER PUBLICATIONS

Sawant, et al., "Segmented phosphors: MEMS-based high quantum efficiency detectors for megavoltage x-ray imaging", Med Phys., 2005.

*Primary Examiner* — Jurie Yun
(74) *Attorney, Agent, or Firm* — Larry Liberchuk

(57) ABSTRACT

The grating device (1) for an X-ray imaging device comprises a grating arrangement (10) and an actuation arrangement (20). The grating arrangement (10) comprises a plurality of grating segments (11). The actuation arrangement (20) is configured to move the plurality of grating segments (11) with at least a rotational component between a first position and a second position. In the first position, the grating segments (11) are arranged in the path of an X-ray beam (30), so that the grating segments (11) influence portions of the X-ray beam (30). In the second position, the grating segments (11) are arranged outside the portions of the path of an X-ray beam (30), so that the portions of the X-ray beam (30) are unaffected by the grating segments (11).

11 Claims, 4 Drawing Sheets

(51) Int. Cl.
 G21K 1/10 (2006.01)
 A61B 6/06 (2006.01)
 G21K 1/02 (2006.01)
 A61B 6/03 (2006.01)
 G01N 23/20 (2018.01)

(52) U.S. Cl.
 CPC ............... G21K 1/10 (2013.01); A61B 6/032 (2013.01); A61B 6/502 (2013.01); G01N 23/20075 (2013.01); G21K 1/025 (2013.01); G21K 2207/005 (2013.01)

(58) Field of Classification Search
 USPC ............. 378/36, 62, 114, 115, 116, 147, 154
 See application file for complete search history.

(56) References Cited

U.S. PATENT DOCUMENTS

| | | |
|---|---|---|
| 7,012,266 B2 | 3/2006 | Jin |
| 7,205,548 B2 | 4/2007 | Pang et al. |
| 7,889,838 B2 | 2/2011 | David et al. |
| 8,565,371 B2 | 10/2013 | Bredno |
| 9,036,773 B2 | 5/2015 | David et al. |
| 9,179,883 B2 | 11/2015 | Spahn |
| 9,287,017 B2 | 3/2016 | Koehler et al. |
| 9,597,050 B2 | 3/2017 | Roessl et al. |
| 9,649,082 B2 | 5/2017 | Wischmann et al. |
| 9,717,470 B2 | 8/2017 | Martens et al. |
| 9,750,465 B2 | 9/2017 | Engel et al. |
| 9,761,021 B2 | 9/2017 | Koehler et al. |
| 2005/0117707 A1 | 6/2005 | Baier et al. |
| 2010/0061511 A1 | 3/2010 | Heid |
| 2010/0119041 A1 | 5/2010 | Ohara |
| 2010/0220832 A1 | 9/2010 | Ning et al. |

GRATING DEVICE FOR AN X-RAY IMAGING DEVICE

CROSS REFERENCE TO RELATED APPLICATIONS

This application is the U.S. National Phase application under 35 U.S.C. § 371 of International Application No. PCT/EP2015/066554, filed Jul. 20, 2015, published as WO2016/020178 on Feb. 11, 2016, which claims the benefit of European Patent Application Number 14179793.6 filed Aug. 5, 2014. These applications are hereby incorporated by reference herein.

FIELD OF THE INVENTION

The invention relates to a grating device for an X-ray imaging device, an interferometer unit, an X-ray imaging system, an X-ray imaging method, and a computer program element for controlling such device and a computer readable medium having stored such computer program element.

BACKGROUND OF THE INVENTION

When acquiring an X-ray image, an object to be examined, e.g. a patient, is arranged between an X-ray generating device and an X-ray detector. X-ray radiation emanating from the X-ray generating device is penetrating the object to be examined, subsequently arriving at the X-ray detector. The object to be examined, situated in the path of the X-ray radiation is spatially attenuating the X-ray beam, depending on the specific tissue structure within the object. The X-ray detector is subsequently detecting the spatially attenuated X-ray radiation by determining an intensity distribution of the X-ray radiation, which image information is employed for generating, further processing, and subsequently displaying an X-ray image of the object to be examined.

However, an object to be examined may provide only minor differences when attenuating the X-ray radiation, resulting in a relatively uniformly attenuated X-ray image having low contrast, thus lacking detail of the imaged inner structure of the object.

While certain objects or regions within an object may comprise similar attenuation properties, a phase of X-ray radiation penetrating the object may be influenced to a larger extent by the structure of the object.

In phase-contrast imaging, at least partly coherent X-ray radiation is employed, e.g., generated by a source grating arranged adjacent to, in the vicinity of an X-ray source, e.g. an X-ray tube. Coherent X-rays penetrating the object may allow for subsequent retrieval of phase information.

However, a phase of a wave cannot be measured directly, rather a phase-shift may be required to be converted to an intensity modulation, e.g., by interfering two or more waves. For generating an according interference pattern, a so-called phase grating is employed, arranged between the object to be examined and an X-ray detector. However, an interference pattern generated by only employing a phase grating may be too small to be detectable with a current X-ray detector, due to a lack of spatial resolution of the X-ray detector.

Thus, a further analyzer grating may be employed arranged between the phase grating and the X-ray detector, subsequently providing an interference pattern, which is large enough to be detectable by current X-ray detectors.

Employing such gratings, in addition to the generation of differential phase-contrast image data, the generation of image data deriving from de-coherent X-ray scatter is enabled, the latter type of imaging also being referred to as "dark-field imaging".

WO 2012/029005 A1 discloses an apparatus for phase-contrast imaging comprising an X-ray source, a first grating element, a second grating element and an X-ray detector element comprising a plurality of detector pixel elements. An object to be imagined is arrangeable between the X-ray source and the X-ray detector element. The first grating element as well as the second grating element is arrangeable between the X-ray source and the X-ray detector element. The X-ray source, the first grating element, the second grating element and the X-ray detector are operatively coupled for acquisition of a phase-contrast image of the object.

However, such imaging device can be still improved, in particular in view of an imaging device, in which the differential phase-contrast imaging can be easily switched on and off.

SUMMARY OF THE INVENTION

Hence, there may be a need to provide an improved grating device for an X-ray imaging device, which allows a differential phase-contrast imaging to be easily switched on and off.

The problem of the present invention is solved by the subject-matters of the independent claims, wherein further embodiments are incorporated in the dependent claims. It should be noted that the aspects of the invention described in the following apply also to the grating device for an X-ray imaging device, an interferometer unit, an X-ray imaging system, an X-ray imaging method, a computer program element, and a computer readable medium.

According to the present invention, a grating device for an X-ray imaging device comprising an X-ray source arrangement configured to provide an X-ray beam is presented. The grating device comprises a grating arrangement and an actuation arrangement. The grating arrangement comprises a plurality of grating segments. The actuation arrangement is configured to move the plurality of grating segments with at least a rotational component between a first position and a second position. In the first position, the grating segments are arranged during operation in the path of an X-ray beam, so that the grating segments influence respective portions of the X-ray beam for the purpose of differential phase-contrast imaging and/or dark-field imaging. In the second position, the grating segments are arranged outside these portions of the path of an X-ray beam, so that these portions of the X-ray beam are unaffected by the grating segments for the purpose of attenuation imaging. The grating device furthermore comprises an X-ray anti-scatter grid or an X-ray collimator, provided with blades, wherein (i) the actuation arrangement and/or the grating segments, when being in the second position, are integrated in said blades; (ii) at least a subset of said blades comprises recesses configured to accommodate the actuation arrangement and/or the grating segments when being in the second position; and/or (iii) the actuation arrangement and the grating segments, when being in the second position, are positioned behind or in front of said blades along the direction of the X-ray beam so that the portions of the X-ray beam are unaffected by the actuation units and the grating segments.

Thereby, the grating device according to the invention allows for easily switching on and off differential phase-contrast imaging (DPCI) in an X-ray imaging device. In other words, the grating device according to the invention provides a practical option to use differential phase-contrast imaging and/or dark-field imaging in addition (or not) to conventional attenuation imaging and thereby provides a flexibility for the clinician to choose between a phase-contrast and/or dark-field exam and a normal exam. This is achieved by moving, with at least a rotational component, the grating segments in and out of the path of the X-ray beam by the actuation arrangement. The introducing and removing of the grating segments relative to the X-ray beam is realized without compromising in any way the imaging. This is achieved as the grating device according to the invention allows covering the entire X-ray detector area with grating arrangements in an essentially gapless manner, i.e., no mounting structures or the like disturb the continuous sampling of X-rays to avoid reconstruction errors and consequent image artifacts. The actuation arrangement and/or the grating segments can be arranged at a front or at a back end of the blade or somewhere between two adjacent blades (when seen in the direction of the X-rays). Exemplarily, in a micro dose slit scanning mammography system, a pre-collimator on a first side of a breast and a post-collimator on a second side of the breast and in front of strip detector lines are used. Both collimators are provided with a slit structure, in which only the slits or illumination windows allow a passage of the X-rays. The actuation arrangement or MEMS and the grating segments in the second position can be integrated into the blades or stripes of the post-collimator and can be thereby hidden from the primary X-ray beam. In the first position, the grating segments are then moved or flipped into the illumination windows, so that the grating segments cover the slits between the blades and influence portions of the X-ray beam. The blades may be structures of a one-dimensional anti-scatter grid, typically made of a strongly attenuating material, as e.g. tungsten. In a "DPCI—off" position, the MEMS gratings are not illuminated and fringes are not detected, even though they can be present in case the phase-grating arrangement and the source grating arrangement are left in the X-ray beam. In the "DPCI—on" position, the analyzer grating arrangement is in the X-ray beam and the differential phase-contrast imaging is active. The integration into blades allows hiding the entire structure and protecting it from unwanted radiation in the "DPCI—off" position. In all cases, X-ray collimator, X-ray anti-scatter grid and else, the term "integrated" may be defined in that the actuation arrangement and/or the grating segments can be accommodated or arranged in recesses of at least a subset of blades in the second position. In other words, some blades may comprise at least one recess with dimensions configured for accommodating an actuation arrangement and/or a grating segment in the second position. The recess may extend over a part or the entire length of a blade. The recess may be a continuous recess or a segmented, discontinuous recess.

The present invention allows for useful application in a clinical environment. More specifically, the present invention is very suitable for application in imaging modalities such as mammography, diagnostic radiology, interventional radiology and computed tomography (CT). In addition, the presentation invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

In an example, the moving of the grating segments is performed locally, that is, each of the plurality of the grating segments is being moved on an individual (yet possibly simultaneous) basis. More specifically, in this example, the actuation arrangement is configured for moving each of the grating segments from the first position to the second position (and vice versa) via a rotation. For this purpose, each of the plurality of grating segments is provided with an individual axis of rotation. Such individual axis of rotation may be comprised in the respective grating segment in order to enable miniaturization. Alternatively, yet equally effective from a miniaturization point of view, the individual axis of rotation is mounted to either surface of the grating segment. Thus, in this example, the plurality of grating segments when being moved from the first to the second position (and vice versa) change orientation relative to the X-ray beam or a respective portion thereof, however, the individual axes of rotation do not change position relative to the X-ray beam or a respective portion thereof. As a result of that, the grating device according to this example effectively circumvents employing a second position in which the plurality of grating segments is located in its entirety outside of the X-ray imaging device's field-of-view. Consequently, the grating device according to this example accomplishes switching from first to second position (and vice versa) employing a minimum amount of movement. Therefore the grating device according to this example is capable of realizing such switching in a minimum amount of time thereby enhancing clinical flexibility indeed.

The grating device according to the invention further allows for easy switching on and off DPCI for X-ray imaging modalities for which large X-ray detector coverage is important. Large X-ray detector coverage may be related to a detector area between 500 and 1500 cm2, preferably between 700 and 1300 cm2 and more preferably between 900 and 1100 cm2. Large X-ray detector coverage is e.g. important for computed tomography (CT) and mammography.

In an example, the actuation arrangement is configured to tilt the grating segments between the first position and the second position, preferably by about 90 degrees. In other words, the movement of one of the plurality of grating segments with at least a rotational component may be a tilt, pivot, rotate or flip movement. The movement may also comprise a translational component, which means the movement is a combination of rotation and translation. In other words, the movement of one of the plurality of grating segments may be a combination of tilting and displacing. Exemplarily, a grating segment can be first lifted and then rotated. The grating segment can also be first moved laterally (perpendicular to the X-ray beam) and then rotated. This lateral movement can also be used to effect a phase stepping. The movement can be two or three dimensional. The result of the movement is a change of the position and/or orientation of the grating segments relative to the X-ray beam.

In an example, the actuation arrangement comprises a plurality of actuation units. All or a subset of the actuation units can be driven by one common drive shaft with a common rotational axis. Alternatively, each or a subset of the actuation units can be driven individually and directly by a plurality of drive shafts. In an example, at least one of the actuation units comprises a micro-electro-mechanical system (MEMS). MEMS can be made up of components between 1 to 100 µm in size (i.e. 0.001 to 0.1 mm). Exemplarily, the MEMS has a size between 50 and 1000 µm, more preferably a size between 100 and 500 µm. Exemplarily, the MEMS structure sizes are compatible with the pixels sizes of computed tomography or mammography. The MEMS may comprise a central unit that processes data and at least a micro component that interacts with the surroundings, such as an actuators and/or a sensor. The MEMS may be manufactured e.g. by deposition processes, lithography, etching, sputtering, etc. The MEMS may be actuated electrostatically or magnetically. The advantage of using MEMS is that no large translation of detector sized gratings structures is required, but single pixel sized gratings structures can be flipped out of the X-ray path.

The grating arrangement comprises a plurality of grating segments, which can be arranged adjacent to each other perpendicular to an X-ray beam. Each grating segment may comprise a grating structure of a respective transmission characteristic. For example, the grating structure comprises lines arranged as a sort of linear stripes of a respective transmission characteristic. With the term "transmission characteristic" absorption properties and/or properties in view of a phase shift are meant. The grating structure may form a plurality of bars and gaps arranged periodically. The bars may be arranged to change a phase and/or amplitude of an X-ray radiation. The gaps may change a phase and/or amplitude of an X-ray radiation to another, in particular lesser degree than the bars. The gaps may be X-ray transparent. The term "X-ray transparent" means that X-ray radiation passing is not changed in its phase and not changed in its amplitude, both to a measurable or reasonable amount. In an example, the grating arrangement is a source grating arrangement G0, a phase grating arrangement G1 and/or an analyzer grating arrangement G2. It is noted that the terms "source grating", "absorber grating" and "phase grating" relate to the function of the grating in terms of their effect on the passing X-ray radiation. However, the terms in a certain sense may also relate to the location or position within an interferometer used for phase contrast imaging.

Exemplarily, the option to switch differential phase-contrast imaging on and off is realized by a flipping of only the analyzer grating arrangement. Flipping out of the phase-grating arrangement and the source grating arrangement is not necessarily required to turn-off the differential phase-contrast imaging. The phase-grating arrangement absorbs only very little radiation, while the source grating arrangement absorbs a lot, but is positioned before the patient (when seen in the direction of the X-rays). Further, the source grating arrangement can be removed by other means, e.g. by sliding it out of the field of view, as it is much smaller than the analyzer grating arrangement and as it is arranged at a location where the X-ray beam is collimated to a few square-centimeters only.

Exemplarily, the switching of a differential phase-contrast imaging on and off is realized even more effectively by flipping the analyzer grating arrangement and the source grating arrangement in sync. Then, two grating devices according to the inventions can be used, one for the analyzer grating arrangement and one for the source grating arrangement.

In an example, the grating arrangement further comprises a control unit configured to control the actuation arrangement to move the grating segments simultaneously or independently from each other. The actuation can be controlled in various ways. The actuation can affect the entire X-ray detector simultaneously, or only certain detector lines or even individual detector pixel can be affected. Further, means can be put in place to guarantee a certain accuracy and reproducibility in the positioning of e.g. the analyzer grating arrangement by the actuation arrangement to perform a phase-acquisition with a well-defined relative offset between the periodic structures of the phase-grating arrangement relative to the analyzer grating arrangement. In an example, the grating segments correspond to portions of the X-ray beam.

According to the present invention, also an interferometer unit is presented. The interferometer unit comprises the grating device and an X-ray detector. The X-ray detector is configured to detect the X-ray beam passing the grating device.

The interferometer unit according to the invention may be part of an X-ray imaging system, which is a CT system or a (slit scanning) mammography system. The grating device according to the invention may also be part of a differential phase-contrast X-ray imaging system.

The X-ray detector may be a scintillator or a direct conversion detector. In an example, the detector is a large coverage detector, which means a detector with a detector area between 500 and 1500 $cm^2$, preferably between 700 and 1300 $cm^2$ and more preferably between 900 and 1100 $cm^2$.

In an example, the grating segment is a grating row, whose size corresponds essentially to the size of a row of pixels of the X-ray detector. In another example, the grating segment is a grating pixel, whose size corresponds essentially to a pixel size of the X-ray detector. The actuation arrangement or MEMS may actuate grating segments of an individual pixel or a group of pixels and, hence, add grating segments or flip them out of the local X-ray beam.

According to the present invention, also an X-ray imaging system is presented. The X-ray imaging system may provide a control of a use of grating-based, differential phase contrast imaging in an X-ray imaging device, e.g., for medical imaging. The X-ray imaging system comprises the interferometer and an X-ray source arrangement. The X-ray source arrangement is configured to provide an X-ray beam to pass through the interferometer unit.

The X-ray source arrangement may comprise an X-ray source and a source grating arrangement. In an example, the X-ray imaging system is a CT system or a mammography system with a differential phase-contrast X-ray imaging option. The X-ray imaging system can be used in diagnostic systems like CT, interventional X-ray systems, mammography systems and general x-ray systems employing large area X-ray detectors.

According to the present invention, also an X-ray imaging method is presented. It comprises the following steps, not necessarily in this order:

Providing a bi-functional option for an X-ray imaging by a grating device comprising an actuation arrangement and a grating arrangement. The grating arrangement comprises a plurality of grating segments and the actuation arrangement is configured to move the plurality of grating segments with at least a rotational component between a first position and a second position. In a first option, the grating segments are arranged in the first position in the path of an X-ray beam, so that the grating segments influence portions of the X-ray beam for the first imaging method. In a second option, the grating segments are arranged in the second position outside the portions of the path of an X-ray beam, so that the portions of the X-ray beam is unaffected by the grating segments for the second imaging method.

Deciding between the first and the second option.

Performing one of the options.

Thereby, the X-ray imaging method allows flexibility for the radiologist to choose between a phase-contrast exam and a normal exam. Exemplarily, the movement of one of the plurality of grating segments with at least a rotational component may be a tilt, pivot, rotate or flip movement. The movement may also comprise a translational component for e.g. a phase stepping. Exemplarily, the actuation arrangement is at least one actuator of a MEMS. Exemplarily, the option to switch differential phase-contrast imaging on and off is realized by a flipping of only the analyzer grating arrangement. Exemplarily, in the second position, the actuation arrangement and the grating segments are integrated into blades of a collimator or into blades of an anti-scatter grid.

According to the present invention, also a computer program element is presented, wherein the computer program element comprises program code means for causing an X-ray imaging device as defined in the independent device claim to carry out the steps of the X-ray imaging method when the computer program is run on a computer controlling the X-ray imaging device.

It shall be understood that the X-ray imaging device, the X-ray imaging system, the X-ray imaging method, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

The gist of the invention may be the use of Micro-Electro-Mechanical Systems (MEMS) to actuate grating hardware of an individual X-ray detector pixel or group of X-ray detector pixels and hence add gratings or flip them out of the local X-ray beam.

The present invention allows for useful application in a clinical environment such as a hospital. More specifically, the present invention is very suitable for application in imaging modalitiesm, including without limitation mammography, for the medical examination of patients. In addition, the presentation invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
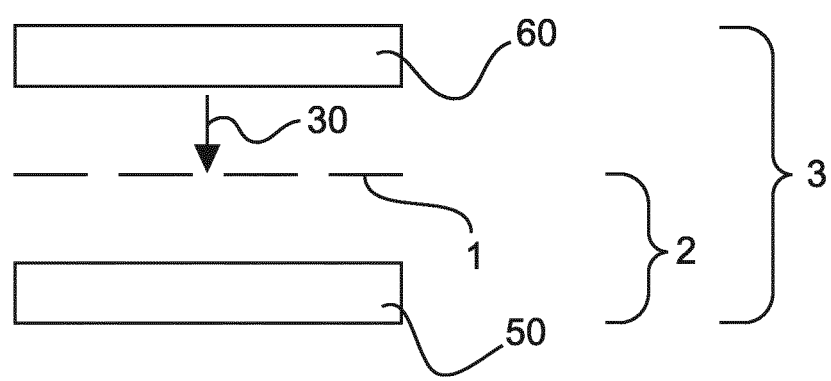
FIG. 1 shows a schematic drawing of an example of a grating device, an interferometer unit and an X-ray imaging system according to the invention.

FIG. 1 shows schematically and exemplarily an embodiment of a grating device 1, an interferometer unit 2 and an X-ray imaging system 3 according to the invention. The X-ray imaging system 3 may provide a control of a use of grating-based, differential phase contrast imaging, e.g., for medical imaging. The X-ray imaging system 3 can be used in diagnostic systems like CT, interventional X-ray systems, mammography systems and general X-ray systems employing large area X-ray detectors.

The X-ray imaging system 3 comprises the interferometer unit 2 and an X-ray source arrangement 60. The X-ray source arrangement 60 provides an X-ray beam 30 to pass through the interferometer unit 2. The interferometer unit 2 comprises the grating device 1 and an X-ray detector 50. X-rays are impinging on the detector surface from top. The X-ray detector 50 detects the X-ray beam 30 passing the grating device 1. The X-ray detector 50 may be a large coverage detector, which means a detector with a detector area between 500 and 1500 $cm^2$.

Figure 2A:
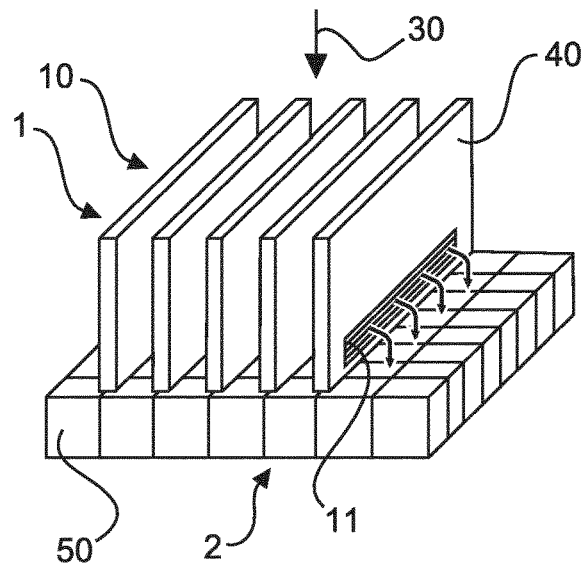
FIGS. 2a, 2b, and 2c show schematically and exemplarily embodiments
Figure 2B:
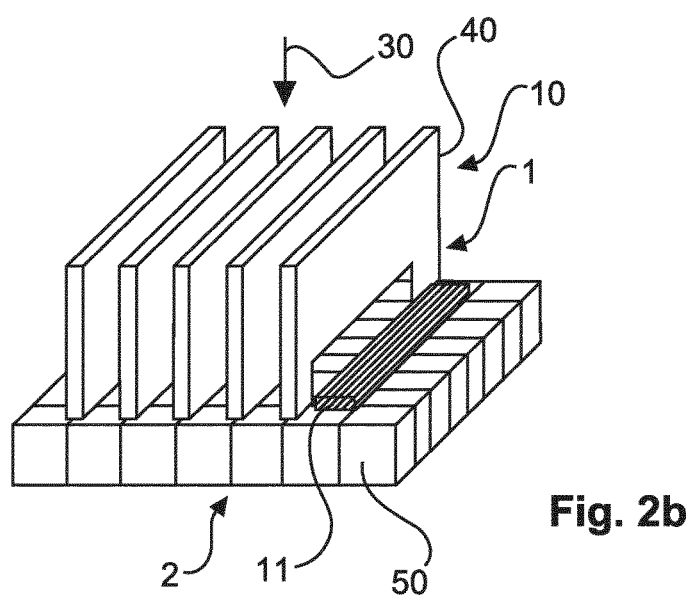
Figure 2C:
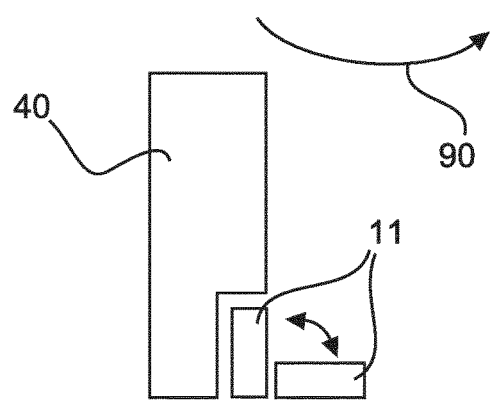

FIGS. 2a, 2b, and 2c show schematically and exemplarily embodiments of the interferometer unit 2 according to the invention. The interferometer unit 2 comprises the grating device 1 and the X-ray detector 50. The shown boxes of the X-ray detector 50 denote individual detector pixels which can be scintillators or direct conversion detectors. The grating device 1 is here an analyzer grating. The interferometer unit 2 further comprises a phase grating (not shown) arranged upstream of the analyzer grating with regard to the X-ray beam 30.

The grating device 1 comprises a grating arrangement 10 and an actuation arrangement 20 (not shown). The grating arrangement 10 comprises a plurality of grating segments 11, which can be arranged adjacent to each other perpendicular to an X-ray beam 30. Each grating segment 11 may comprise a grating structure of a respective transmission characteristic. The grating arrangement 10 is here an analyzer grating arrangement, but may also or instead be a phase grating arrangement and/or a source grating arrangement.

The actuation arrangement 20 comprises here at least one actuation unit comprising a MEMS. Each actuation unit is configured to move one of the plurality of grating segments 11 with at least a rotational component between a first position and a second position. The movement may be a tilt, pivot, rotate or flip movement. The movement may also comprise a translational component for e.g. phase stepping, which means the movement of one of the plurality of grating segments 11 may be a combination of tilting and displacing. The result of the movement is a change of the position and/or orientation of the grating segments 11 relative to the X-ray beam 30.

In FIGS. 2a and 2b, the switching of the differential phase-contrast imaging on and off is realized by flipping only the analyzer grating arrangement 10. The MEMS actuation on the analyzer grating arrangement 10 is indicated in FIG. 2a by four black arrows. Flipping out of the phase-grating arrangement and the source grating arrangement is not necessarily required to turn-off the differential phase-contrast imaging.

In the first position, shown in FIG. 2b, the grating segment 11 is arranged in the path of an X-ray beam 30, so that the grating segment 11 influences at least portions of the X-ray beam 30. In the second position, shown in FIG. 2a, the grating segment 11 is arranged outside the portions of the path of an X-ray beam 30, so that the portions of the X-ray beam 30 are unaffected by the grating segment.

In FIG. 2a, in the second position, the actuation arrangement 20 (not shown) and the grating segment 11 are integrated into a blade 40 of an anti-scatter grid. The blades 40 are here structures of a one-dimensional anti-scatter grid, typically made of a strongly attenuating material. One blade is singled out for illustration. The blades 40 to the right of it are left out for the purpose of illustration. The term "integrated" means that the actuation arrangement 20 and the grating segment 11 are accommodated in a recess within the blade and shielded from X-ray irradiation from the top. The actuation arrangement 20 (not shown) is arranged at the lower end of the anti-scatter grid. In this so-called "DPCI—off" position, the grating segment 11 is not illuminated and fringes are not detected, even though they can be present in case the phase-grating arrangement and the source grating arrangement are left in the X-ray beam 30.

In FIG. 2b, in the first position, the grating segment 11 is arranged between two adjacent blades 40 perpendicular to the X-ray beam 30 to cover the slit between the two blades 40. In this so-called "DPCI—on" position, the analyzer grating arrangement 10 lies in the X-ray beam 30 and the differential phase-contrast imaging is active.

In this example each of the grating segments 11 is provided with an individual axis of rotation. In this example, such individual axis of rotation is mounted to—seen along the direction of the X-ray beam 30—to the bottom surface of the grating segment 11. Each actuation unit is configured to rotate a respective grating segment 11 with respect to its individual axis of rotation from the first to the second position (and vice versa).

FIG. 2c shows a blade 40 of an anti-scatter grid and an integrated grating segment 11, here a part of an analyzer grating. Arrow 90 shows the rotation or direction of a CT system. When the CT starts turning in the rotation direction 90, the grating segment 11 in the upright or off-position is supported by a part of the blade 40 to withstand the acceleration force. In its horizontal or on-position, the grating segment 11 is supported by an X-Ray detector (not shown) arranged below that absorbs the centripetal forces on the analyzer grating segment 11. Preferably, the switching between the off and the on-position is not effected during the rotation of the CT system.

Figure 3A:
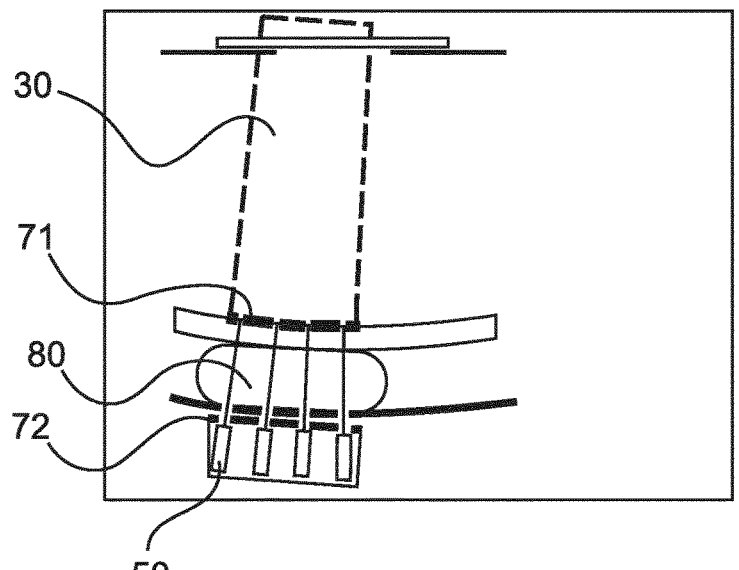
FIG. 3a shows schematically and exemplarily a slit scanning mammography system and FIGS. 3b and 3c show details thereof with an exemplary grating device 1 according to the invention.
Figure 3B:
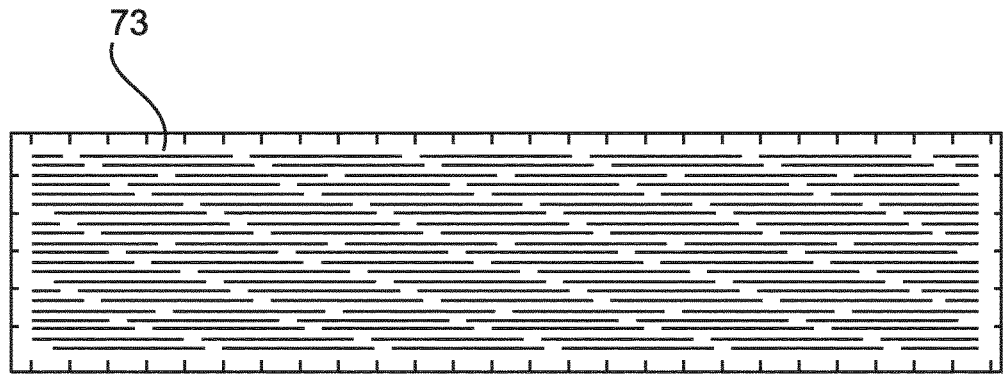
Figure 3C:
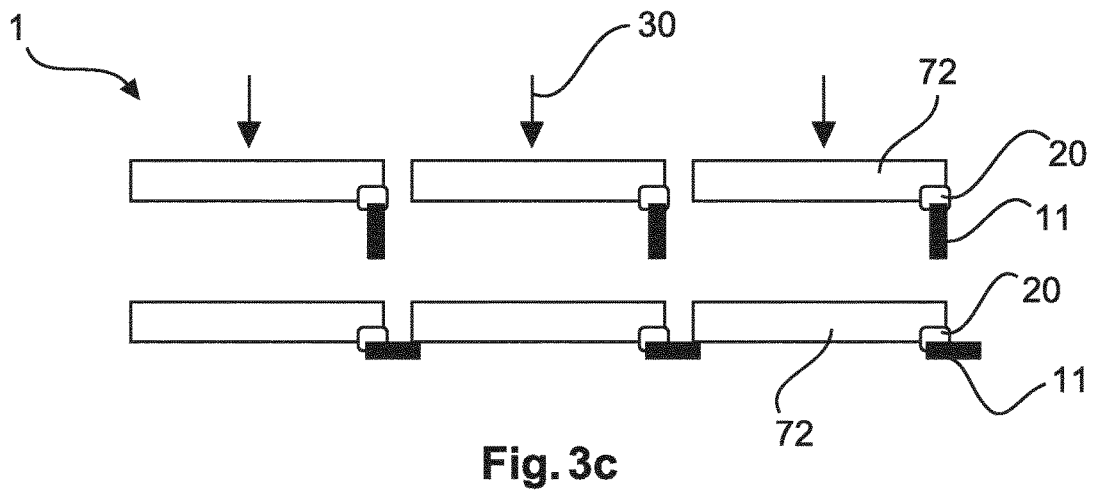

FIG. 3a shows schematically and exemplarily a slit scanning mammography system and FIGS. 3b and 3c show details thereof with an exemplary grating device 1 according to the invention. A pre-collimator 71 is arranged on a first side of a breast 80 and a post-collimator 72 is arranged on a second side of the breast 80 and in front of strip detector lines of an X-ray detector 50. Both collimators 71, 72 are provided with a slit structure as shown in FIG. 3b, in which only the slits or illumination windows 73 allow a passage of the X-rays. As shown in FIG. 3c above, single actuation units of the actuation arrangement 20 or MEMS and the grating segments 11 in the second position are positioned close behind the blades of the post-collimator 72 in the direction of the X-ray beam 30 and are thereby hidden from the X-ray beam 30, so that the X-ray beam 30 is unaffected by the grating segments 11. In the first position as shown in FIG. 3c below, the grating segments are then moved or flipped by 90 degrees into the illumination windows 73, so that the grating segments 11 influence portions of the X-ray beam 30. In this example each of the grating segments 11 is provided with an individual axis of rotation. In this example, such individual axis of rotation is mounted to—seen along the direction of the X-ray beam 30—to the bottom surface of the grating segment 11. Each actuation unit is configured to rotate a respective grating segment 11 with respect to its individual axis of rotation from the first to the second position (and vice versa).

Figure 4:
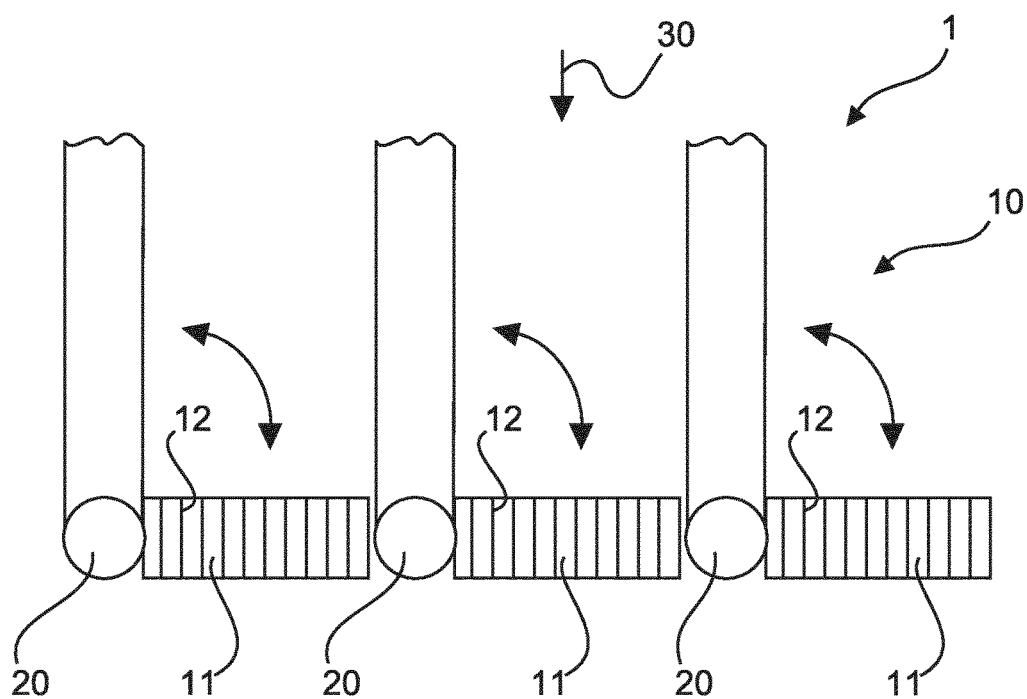
FIG. 4 shows schematically and exemplarily an embodiment of the grating device for an X-ray imaging device according to the invention.

FIG. 4 shows schematically and exemplarily an embodiment of the grating device 1 for an X-ray imaging device comprising a grating arrangement 10 and a plurality of actuation units of the actuation arrangement 20. The grating arrangement 10 comprises a plurality of grating segments 11, which are arranged adjacent to each other perpendicular to an X-ray beam 30. Each grating segment 11 may comprise a grating structure 12 of a respective transmission characteristic. The grating arrangement 10 is here an analyzer grating arrangement 10.

The actuation units of the actuation arrangement 20 in this example comprise MEMS. The MEMS may be actuated electrostatically or magnetically. Each actuation unit is configured to tilt one of the plurality of grating segments 11 with at least a rotational component between a first position and a second position as shown by the arrows. The result of the movement is a change of the position and/or orientation of the grating segments 11 relative to the X-ray beam 30.

Figure 5:
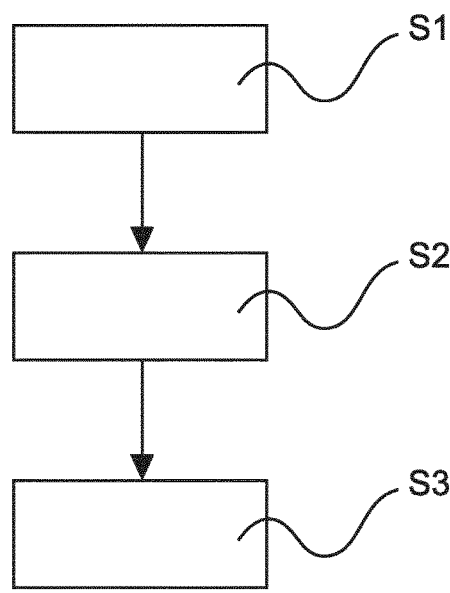
FIG. 5 shows basic steps of an example of an X-ray imaging method according to the invention.

FIG. 5 shows a schematic overview of steps of an X-ray imaging method. The method comprises the following steps, not necessarily in this order:

providing a bi-functional option for an X-ray imaging by a grating device comprising an actuation arrangement (20) and a grating arrangement (10); wherein the grating arrangement (10) comprises a plurality of grating segments (11); and wherein the actuation arrangement (20) is configured to move the plurality of grating segments (11) with at least a rotational component between a first position and a second position;

wherein in a first option, the grating segments 11 are arranged in the first position in the path of an X-ray beam 30, so that the grating segments 11 influence portions of the X-ray beam 30 for the first imaging method;

wherein in a first option, the grating segments 11 are arranged in the first position in the path of an X-ray beam 30, so that the grating segments 11 influence portions of the X-ray beam 30 for the first imaging method;

wherein in a second option, the grating segments 11 are arranged in the second position outside the portions of the path of an X-ray beam 30, so that the portions of the X-ray beam 30 is unaffected by the grating segments 11 for the second imaging method;

deciding between the first and the second option; and performing one of the options.

Thereby, the X-ray imaging method allows flexibility for the radiologist to choose between a phase-contrast exam and a normal exam. The movement of one of the plurality of grating segments 11 with at least a rotational component may be a tilt, pivot, rotate or flip movement. The movement may also comprise a translational component for e.g. a phase stepping. An actuation unit of the actuation arrangement 20 is at least one actuator of a MEMS. An option to switch differential phase-contrast imaging on and off is realized by a flipping of only an analyzer grating arrangement 10. In the second position, the actuation units and the grating segments 11 are integrated into blades of a collimator or into blades 40 of an anti-scatter grid.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A grating device for an X-ray imaging device comprising an X-ray source arrangement configured to provide an X-ray beam, comprising:

a grating arrangement;

an actuation arrangement;

wherein the grating arrangement comprises a plurality of grating segments;

wherein the actuation arrangement is configured to move the plurality of grating segments with at least a rotational component between a first position and a second position;

wherein in the first position the grating segments are arranged during operation in a path of the X-ray beam, so that the grating segments influence portions of the X-ray beam for the purpose of differential phase-contrast imaging and/or dark-field imaging; and wherein in the second position the grating segments are arranged during operation outside the portions of the path of the X-ray beam, so that the portions of the X-ray beam are unaffected by the grating segments for the purpose of attenuation imaging; and an X-ray anti-scatter grid or an X-ray collimator provided with blades, wherein (i) the actuation arrangement and/or the grating segments, when being in the second position, are integrated in said blades; (ii) at least a subset of said blades comprises recesses configured to accommodate the actuation arrangement and/or the grating segments when being in the second position; and/or (iii) the actuation arrangement and the grating segments, when being in the second position, are positioned behind or in front of said blades along the direction of the X-ray beam so that the portions of the X-ray beam are unaffected by the actuation arrangement and the grating segments.

2. The grating device according to claim 1, wherein the actuation arrangement is configured to tilt the grating segments between the first position and the second position.

3. The grating device according to claim 1, wherein the grating arrangement is one of an analyzer grating arrangement, a phase grating arrangement, and a source grating arrangement.

4. The grating device according to claim 1, wherein the actuation arrangement comprises a plurality of actuation units; and wherein at least one actuation unit comprises a micro-electro-mechanical system.

5. The grating device according to claim 1, further comprising a control unit configured to control the actuation arrangement to move the grating segments simultaneously or independently from each other.

6. An interferometer unit, comprising:

the grating device according to claim 1; and an X-ray detector, wherein the X-ray detector is configured to detect the X-ray beam passing the grating device.

7. The interferometer unit according to claim 6, wherein a grating segment of the grating device is a grating pixel wherein a size of the grating pixel corresponds substantially to a pixel size of the X-ray detector, or the grating segment is a grating row wherein a size of the grating row corresponds substantially to the size of a row of pixels of the X-ray detector.

8. An X-ray imaging system, comprising:
the interferometer unit according to claim 6; and
an X-ray source arrangement, wherein the X-ray source arrangement is configured to provide an X-ray beam to pass through the interferometer unit.

9. The X-ray imaging system according to claim 8, wherein the X-ray imaging system is one of a CT system, a mammography system, a diagnostic X-Ray system, and an interventional X-Ray system.

10. An X-ray imaging method, comprising:
providing a bi-functional option for switching between (i) differential phase-contrast imaging and/or dark-field imaging; and (ii) attenuation imaging by way of a grating device comprising an actuation arrangement and a grating arrangement; wherein the grating arrangement comprises a plurality of grating segments; and wherein the actuation arrangement is configured to move the plurality of grating segments with at least a rotational component between a first position and a second position; wherein in a first option; the grating segments are arranged in the first position in the path of an X-ray beam, so that the grating segments influence portions of the X-ray beam for the first imaging method; wherein in a second option; the grating segments are arranged in the second position outside the portions of the path of the X-ray beam, so that the portions of the X-ray beam are unaffected by the grating segments for the second imaging method; and furthermore comprising an X-ray anti-scatter grid or an X-ray collimator; provided with blades, wherein (i) the actuation arrangement and/or the grating segments, when being in the second position, are integrated in said blades;
(ii) at least a subset of said blades comprises recesses configured to accommodate the actuation arrangement and/or the grating segments when being in the second position; and/or
(iii) the actuation arrangement and the grating segments, when being in the second position, are positioned behind or in front of said blades along the direction of the X-ray beam so that the portions of the X-ray beam are unaffected by the actuation arrangement and the grating segments;

deciding between the first and the second option; and
performing one of the options.

11. A non-transitory computer-readable medium having one or more executable instructions stored thereon, which when executed by a processor, cause the processor to perform a X-ray imaging method, comprising:
providing a bi-functional option for switching between (i) differential phase-contrast imaging and/or dark-field imaging; and (ii) attenuation imaging by way of a grating device comprising an actuation arrangement and a grating arrangement; wherein the grating arrangement comprises a plurality of grating segments; and wherein the actuation arrangement is configured to move the plurality of grating segments with at least a rotational component between a first position and a second position; wherein in a first option the grating segments are arranged in the first position in the path of an X-ray beam, so that the grating segments influence portions of the X-ray beam for the first imaging method; wherein in a second option the grating segments are arranged in the second position outside the portions of the path of the X-ray beam, so that the portions of the X-ray beam are unaffected by the grating segments for the second imaging method; and furthermore comprising an X-ray anti-scatter grid or an X-ray collimator provided with blades, wherein (i) the actuation arrangement and/or the grating segments, when being in the second position, are integrated in said blades; (ii) at least a subset of said blades comprises recesses configured to accommodate the actuation arrangement and/or the grating segments when being in the second position; and/or (iii) the actuation arrangement and the grating segments, when being in the second position, are positioned behind or in front of said blades along the direction of the X-ray beam so that the portions of the X-ray beam are unaffected by the actuation arrangement and the grating segments;

deciding between the first and the second option; and
performing one of the options.

* * * * *